US00PP09929P

United States Patent [19]

Noodelijk

[11] Patent Number: Plant 9,929

[45] Date of Patent: Jun. 17, 1997

[54] CHRYSANTHEMUM PLANT NAMED 'DARK RED REAGAN'

[75] Inventor: Robert Noodelijk, Woubrugge, Netherlands

[73] Assignee: Chrysanthemum Breeders Association, N.V., Netherlands

[21] Appl. No.: 642,905

[22] Filed: May 6, 1996

[51] Int. Cl.[6] ..... A01H 5/00

[52] U.S. Cl. ..... Plt./82.5

[58] Field of Search ..... Plt./74.1, 82.5

*Primary Examiner*—Howard J. Locker
*Attorney, Agent, or Firm*—Parkhurst, Wendel & Burr, L.L.P.

[57] ABSTRACT

A new and distinct cultivar of Chrysanthemum plant named Dark Red Reagan, bearing medium sized red blooms with a yellow-green center and performance of 24–28 days.

2 Drawing Sheets

BACKGROUND OF THE INVENTION

The present invention comprises a new and distinct cultivar of Chrysanthemum plant which is a natural occurring sport of a parent chrysanthemum named Reagan. Parent chrysanthemum Reagan is described in U.S. Plant Pat. No. 8,642. The new cultivar was discovered as a whole plant mutation in 1992 in a greenhouse in Holland. Other naturally occurring mutations of 'Reagan' for which U.S. plant patent protection is being sought include the cultivar 'Dark Splendid Reagan' (copending plant patent application Ser. No. 08/642,224) and 'Sunny Reagan' (copending plant patent application Ser. No. 08/642,904).

The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a medium sized bloom and Red color.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
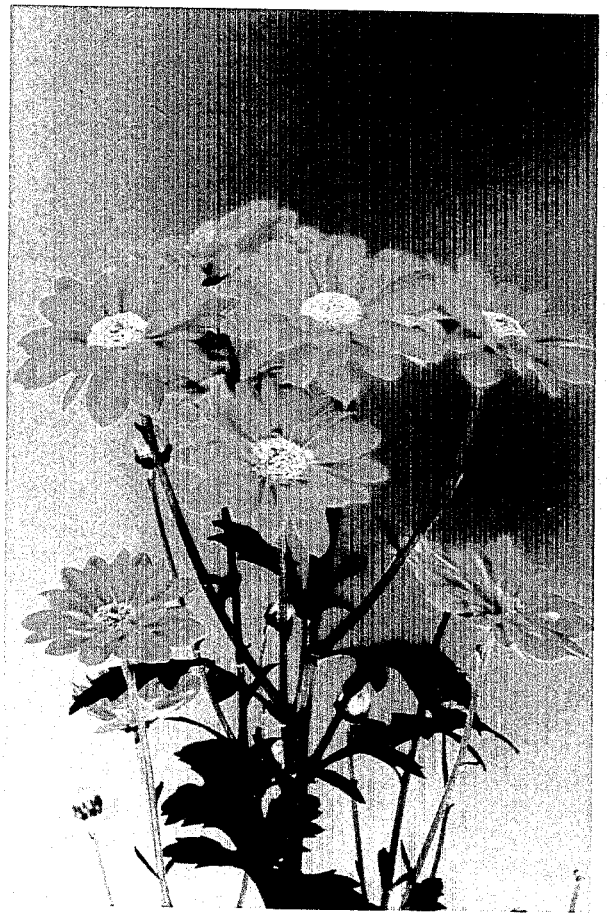
FIG. 1 shows the full bloom of the new cultivar.
Figure 2:
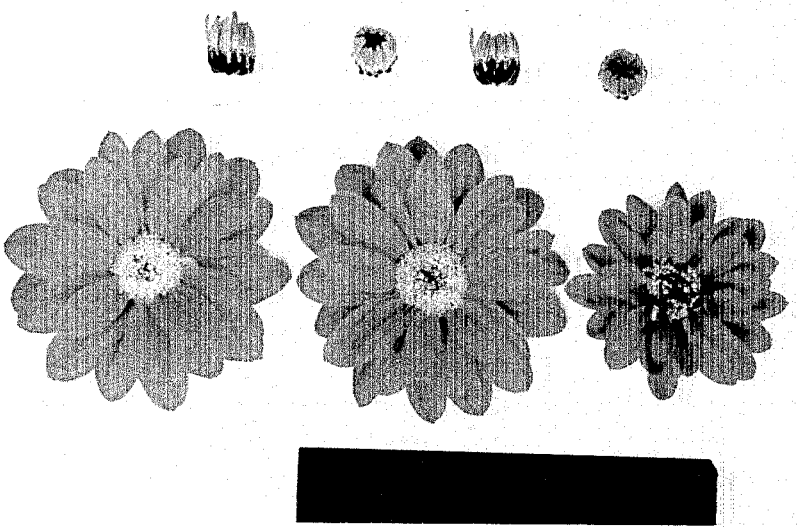
FIG. 2 shows the various stages of bloom of the new cultivar.
Figure 3:
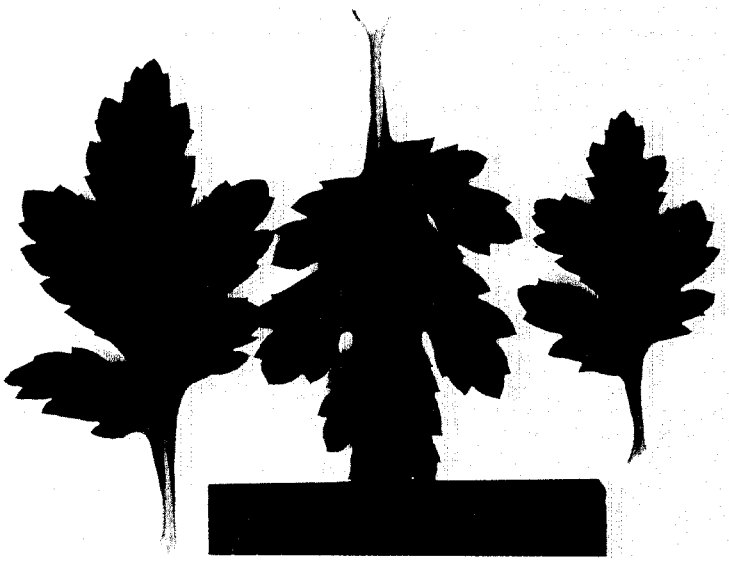
FIG. 3 shows foliage and petiole of the new cultivar.

This new variety of Chrysanthemum is of the botanical classification *Chrysanthemum morifolium*. When grown in the vicinity of Ter Aar, Holland, it has a response time of approximately 7½ weeks. This new variety produces medium sized Red blooms with a yellow-green center having a 4 week performance (i.e., vase life of 24–28 days). This new variety of Chrysanthemum has been found to retain its distinctive characteristics throughout successive propagations and may be planted under greenhouse conditions in Holland between weeks 50 and 35. The following is a description of the plant and characteristics (color designations are from R.H.S. Color Chart) that distinguish it from related known varieties and its antecedents: The color designations are taken from the plant itself. Accordingly, any discrepancies between the color designations and the colors depicted in the photographs are due to photographic tolerances.

Detailed Botanical Description and Comparative Data

| CULTIVAR | Dark Red Reagan | Parent Cultivar Reagan |
|---|---|---|
| Bud | | |
| Size | Medium cross section ±1.0 cm height ±0.7 cm | Medium cross section ±1.0 cm height ±0.7 cm |
| Form | Round and flat | Round and flat |
| Outside Color | Near Greyed Purple 186A | Greyed Purple 186D but paler |
| Bloom | | |
| Size Fully Expanded | Medium 6½–7 cm | Medium 6½–7 cm |
| Borne | Upper portion, single flower per peduncle, lower portion plural flowers per peduncle | Upper portion, single flower per peduncle, lower portion plural flowers per peduncle |
| Peduncle Lengths | Near the top ±14 cm, near the middle ±24 cm, near the bottom ±28 cm | Near the top ±14 cm, near the middle ±24 cm, near the bottom ±28 cm |
| Peduncle Lateral Shoot, Attachment | Weak to medium | medium |
| Peduncle Lateral Shoot, Angle | small | medium |
| Form | Single (Daisy) | Single (Daisy) |
| Performance | Very good 24–28 days (18–20° C.) | Very good 24–28 days (18–20° C.) |
| Color | | |
| Center of Flower | Immature: Yellow-Green 144A Mature: Yellow-Green 154A | Immature: Yellow-Green 151C Mature: Yellow-Green 154A |
| Base of Petals | Unevenly colored; near Greyed-Red 182A lightly streaked with Greyed-Orange 167B | Purple 75B |
| Outer Petals | Unevenly colored; near Greyed-Red 182A lightly streaked with Greyed-Orange | Purple 75B |

-continued

| | | |
|---|---|---|
| | 167B | |
| Inside of Petals | Unevenly colored; near Greyed-Red 182A lightly streaked with Greyed-Orange 167B | Purple 75B |
| Reverse of Petals | Yellow-White 158A tinged with Greyed-Purple 186D between the ribs and towards the margin | Red-Purple 69D but paler |
| Tonality from Distance | A red daisy with a fresh looking center having a little or no pollen | A pale pink daisy with a fresh looking center having a little or no pollen |
| Discoloration | Some to Greyed-Red 181C | Some to Red-Purple 69D |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | convex, two keels | flat, two keels |
| Arrangement | Imbricated | Imbricated |
| Persistance | Good. Petals keep straight or reflex somewhat at the edge at the end of blooming. | Good. Petals keep straight or reflex somewhat at the edge at the end of blooming. |
| Fragrance | Typical Chrysanthemum | Typical Chrysanthemum |
| Disc Diameter | Medium to large (1.5–2.0 cm) | Medium (1.5 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Medium | Strong |
| Height | 100–125 cm | 100–125 cm |
| Stem Color | Yellow-Green 144A | Yellow-Green 144A |
| Stem Strength | Strong | Medium |
| Stem Brittleness | Absent | Present |
| Stem Anthocyanin Coloration | Present, at the base and along the ribs | Absent |
| Internodes | 3 cm | 3 cm |
| Flowering Response | 7½ weeks | 7½ weeks |
| Foliage | | |
| Color | Upperside Green 137A. Underside Green 137C. | Upperside Green 137A. Underside Green 137C. |
| Size | Length ±11 cm. Width ±9 cm. | Length ±12 cm. Width ±9 cm. |
| Quantity | 22–28 | 22–28 |
| Shape | Lobed, see photograph | Lobed, see photograph |
| Texture | Upperside rough, underside smooth, slightly hirsute | Upperside rough, underside smooth, slightly hirsute |
| Ribs and Veins | Ribs well developed. Veins not so developed. | Ribs well developed. Veins not so developed. |

-continued

| | | |
|---|---|---|
| Edge | Crenated | Crenated |
| Shape of Base of Sinus Between Lateral Lobes | Round | Round |
| Margin of Sinus Between Lateral Lobes | Converging | Converging |
| Shape of Base | Cordate | Rounded |
| Apex | Mucronate | Cupsodate |
| Response time | | |
| Difference in days of average response | +1½ | 0 |
| Response to ALAR | | |
| Dose utilized to obtain plant height of about 90 cm (g/100 l $H_2O$) | 300 | 300 |
| Year of Discovery | 1992 | 1986 |

| CULTIVAR | Dark Splendid Reagan | Sunny Reagan |
|---|---|---|
| Bud | | |
| Size | Medium cross section ±1.0 cm height ±0.7 cm | Medium cross section ±1.0 cm height ±0.7 cm |
| Form | Round and flat | Round and flat |
| Outside Color | Near Red-Purple 70A | Between Yellow 7A/Yellow 9A |
| Bloom | Medium | Medium |
| Fully Expanded | 6½–7 cm | 6½–7 cm |
| Borne | Upper portion, single flower per peduncle, lower portion plural flowers per peduncle | Upper portion, flower per peduncle, lower portion plural flowers per peduncle |
| Peduncle Lengths | Near the top ±14 cm, near the middle ±24, cm, near the bottom ±28 cm | Near the top ±14 cm, near the middle ±24 cm, near the bottom ±28 cm |
| Peduncle Lateral Shoot, Attachment | medium | medium |
| Peduncle Lateral Shoot, Angle | small | medium |
| Form | Single (Daisy) | Single (Daisy) |
| Performance | Very good 24–28 days (18–20° C.) | Very good 24–28 (18–20° C.) |
| Color | | |
| | Immature: Yellow-Green 144A Mature: Yellow-Green 154A | Immature: Yellow-Green 144A Mature: Yellow-Green 154A |
| Base of Petals | Near Red-Purple 71C but very slightly more blue | Yellow 5A deepening slightly to Yellow 6A in the basal half |
| Outer Petals | Near Red-Purple 71C but very slightly more blue | Yellow 5A deepening slightly to Yellow 6A in the basal half |
| Inside of Petals | Near Red-Purple 71C but very slightly more blue | Yellow 5A deepening slightly to Yellow 6A in the basal half |
| Reverse of Petals | Nearest Purple-Violet 80D but more grey and with a slightly deeper tonation | Yellow 6A |
| Tonality from Distance | A purple daisy with a fresh looking center having a | A yellow daisy with a fresh looking center having a |

-continued

| | | |
|---|---|---|
| | little or no pollen | little or no pollen |
| Discoloration | Some to Red-Purple 72C | Some to Yellow 5B |
| Pollen | Yellow-Orange 14A | Yellow-Orange 14A |
| Petals | | |
| Texture | Upperside smooth, underside smooth | Upperside smooth, underside smooth |
| Number | 24–30 (two rows) | 24–30 (two rows) |
| Cross-section | convex, no keels | convex, two keels |
| Arrangement | Imbricated | Imbricated |
| Persistence | Good. Petals keep straight or reflex somewhat at the edge at the end of blooming. | Good. Petals keep straight or reflex somewhat at the edge at the the end of blooming. |
| Fragrance | Typical Chrysanthemum | Typical Chrysanthemum |
| Disc Diameter | Medium to large (1.5–2.0 cm) | Medium to large (1.5–2.0 cm) |
| Reproductive Organs | | |
| Stamen | Yellow, thick, 3 mm in length | Yellow, thick, 3 mm in length |
| Pollen | Appears at late stage of blooming | Appears at late stage of blooming |
| Styles | Green, thick | Green, thick |
| Style Length | ±5 mm | ±5 mm |
| Stigmas | Yellow | Yellow |
| Stigma Width | ±1 mm | ±1 mm |
| Ovaries | Enclosed in calyx | Enclosed in calyx |
| Plant | | |
| Form | Spray mum meant for erect culture. Herbaceous. | Spray mum meant for erect culture. Herbaceous. |
| Growth | Medium | Strong |
| Height | 100–125 cm | 100–125 cm |
| Stem Color | Yellow-Green 144A | Yellow-Green 144A |
| Stem Strength | Strong | Strong |
| Stem Brittleness | Absent | Absent |
| Stem Anthocyanin Coloration | Present, at the base and along the ribs | Present, mainly at the base |
| Internodes | 3 cm | 3 cm |
| Flowering Response | 7½ weeks | 7½ weeks |

-continued

| | | |
|---|---|---|
| Foliage | | |
| Color | Upperside Green. 137A. Underside Green 137C. | Upperside Green 137A. Underside Green 137C. |
| Size | Length ±11 cm. Width ±9 cm. | Length ±12 cm. |
| Width ±9 cm. | | |
| Quantity | 22–28 | 22–28 |
| Shape | Lobed, see photograph | Lobes, see photograph |
| Texture | Upperside rough, underside smooth, slightly hirsute. | Upperside rough, underside smooth, slightly hirsute. |
| Ribs and Veins | Ribs well developed. Veins not so developed. | Ribs well developed. Veins not so developed. |
| Edge | Crenated | Crenated |
| Shape of Base of Sinus Between Lateral Lobes | Round | Round |
| Margin of Sinus Between Lateral Lobes | Converging | Converging |
| Shape of Base | Cordate | Truncate |
| Apex | Mucronate | Mucronate |
| Response time | | |
| Difference in days of average response | +1 | +1½ |
| Response to ALAR | | |
| Dose utilized to obtain plant height of about 90 cm (g/100 l $H_2O$) | 300 | 450 |
| Year of Discovery | 1991 | 1991 |

I claim:

1. A new and distinct variety of Chrysanthemum plant as described and illustrated.

* * * * *